(12) United States Patent
Naotsuka et al.

(10) Patent No.: US 7,868,019 B2
(45) Date of Patent: Jan. 11, 2011

(54) DERMATITIS TREATING AGENT

(75) Inventors: Atsuko Naotsuka, Osaka (JP); Matsuo Kikuchi, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 424 days.

(21) Appl. No.: 12/089,295

(22) PCT Filed: Oct. 5, 2006

(86) PCT No.: PCT/JP2006/319932

§ 371 (c)(1),
(2), (4) Date: Apr. 4, 2008

(87) PCT Pub. No.: WO2007/043426

PCT Pub. Date: Apr. 19, 2007

(65) Prior Publication Data

US 2010/0130494 A1    May 27, 2010

(30) Foreign Application Priority Data

Oct. 5, 2005    (JP) ............................. 2005-292040

(51) Int. Cl.
    *A61K 31/47* (2006.01)
    *A61K 31/44* (2006.01)
(52) U.S. Cl. ....................... 514/307; 514/339
(58) Field of Classification Search ............. 514/307, 514/339
See application file for complete search history.

(56) References Cited

U.S. PATENT DOCUMENTS

| 5,965,730 | A | 10/1999 | Ukita et al. |
| 6,005,106 | A | 12/1999 | Ukita et al. |

FOREIGN PATENT DOCUMENTS

| EP | 0 748 805 A1 | 12/1996 |
| EP | 0 848 000 B1 | 6/2002 |
| JP | 9-59255 | 3/1997 |
| JP | 10-226685 | 8/1998 |
| JP | 2000-63275 | 2/2000 |
| JP | 2006-151964 | 6/2006 |
| WO | WO 2004/067006 A1 | 8/2004 |

OTHER PUBLICATIONS

D. Griswold et al., "SB 207499 (Ariflo), a Second Generation Phosphodiesterase 4 Inhibitor, Reduces Tumor Necrosis Factor α and Interleukin-4 Production in vivo," The Journal of Pharmacology and Experimental Therapeutics, vol. 287, No. 2, pp. 705-711 (1998).
A. Ehinger et al., "Effects of the Phosphodiesterase 4 Inhibitor RPR 73401 in a Model of Immunological Inflammation," European Journal of Pharmacology, vol. 392, pp. 93-99 (2000).
W. Baumer et al., "Effects of the Phosphodiesterase 4 Inhibitors SB 207499 and AWD 12-281 on the Inflammatory Reaction in a Model of Allergic Dermatitis," European Journal of Pharmacology, vol. 446, pp. 195-200 (2002).
I. Iwamoto et al., "Role of CD4+ T Lymphocytes and Interleukin-5 in Antigen-Induced Eosinophil Recruitment into the Site of Cutaneous Late-Phase Reaction in Mice," Journal of Leukocyte Biology, vol. 52, pp. 572-578 (Nov. 1992).
E. Frigas et al., "The Eosinophil and the Pathophysiology of Asthma," The Journal of Allergy and Clinical Immunology, vol. 77, No. 4, pp. 527-537 (Apr. 1986).
Supplementary European Search Report and Search Opinion for application EP06811270 based on PCT/JP2006/319932, (2006).
Dyke & Montana, "The therapeutic potential of PDE4 inhibitors," Exp. Opin. Invest. Drugs (1999) 8(9):1301-25.
Kaminuma et al., "A Novel Phosphodiesterase Inhibitor, T-440: Possible Management of Eosinophilic Inflammation by Down-Regulation of Interleukin-5 Production," Int Arch Allergy Immunol. (1996) 111(suppl 1):16-18.

(Continued)

*Primary Examiner*—Raymond J Henley, III
(74) *Attorney, Agent, or Firm*—Finnegan, Henderson, Farabow, Garrett & Dunner, L.L.P.

(57) ABSTRACT

The present invention is to provide a topical dermatitis treating agent which comprises a pyridine compound represented by the following formula [I]:

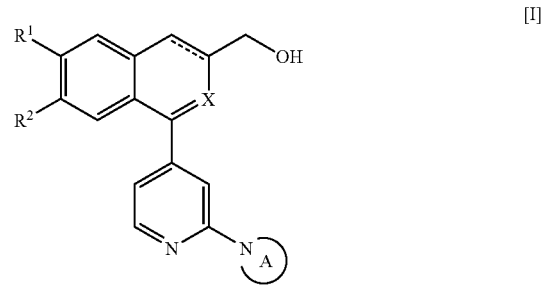

[I]

wherein $R^1$ and $R^2$ each represent a lower alkoxy group, =X— represents a group represented by the formula:

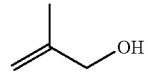

or a group represented by the formula: =N—, Ring A represents a saturated or unsaturated bicyclic nitrogen-containing heterocyclic group having 1 to 4 substituents selected from hydroxyl group, oxo group, a lower alkoxy group, a di-lower alkylaminophenyl group, a pyperidino-lower alkoxy group, a morpholino-lower alkoxy group, a cyclo-lower alkylamino-lower alkylamino group, pyridyl group and morpholino group, and ═══represents a single bond or a double bond, or a pharmaceutically acceptable salt thereof as an active ingredient.

8 Claims, No Drawings

OTHER PUBLICATIONS

De Brito et al., "Type 4 Phosphodiesterase Inhibitors and Their Potential in the Treatment of Inflammatory Disease," Emerging Drugs (1997) 2:249-268.

Ukita et al., "Novel, Potent, and Selective Phosphodiesterase-4 Inhibitors as Antiasthmatic Agents: Synthesis and Biological Activities of a Series of 1-Pyridylnaphthalene Derivatives," J. Med. Chem. (1999) 42:1088-99.

Ukita et al., "Synthesis and Biological Activities of 1-Pyridylisoquinoline and 1-Pyridyldihydroisoquinoline Derivatives as PDE4 Inhibitors," Bioorganic & Medicinal Chemistry Letters (2003) 13:2347-50.

DERMATITIS TREATING AGENT

CROSS-REFERENCE TO RELATED APPLICATIONS

This application is a national phase application of International Application No. PCT/JP2006/319932, filed Oct. 5, 2006, and claims the priority of Japanese Application No. 2005-292040, filed Oct. 5, 2005, the content of both of which is incorporated herein by reference.

TECHNICAL FIELD

The present invention relates to a novel topical agent useful for treatment of dermatitis such as atopic dermatitis and the like.

BACKGROUND ART

Dermatitis is an inflammatory disease at the skin against various kinds of endogenetic and exogenetic invasion, and the disease includes atopic dermatitis, contact dermatitis, seborrheic dermatitis, nummular eczema, autosensitization eczema and the like. These dermatitises accompany itching in many cases. Also, of these, atopic dermatitis is a refractory chronic inflammatory disease which repeats remission and exacerbation, and involvement of a late phase reaction that accompanies invasion of eosinophils or lymphocyte and production of various kinds of cytokines at a site of inflammation has been suggested for pathogeny and chronicity of the disease (Non-Patent Literatures 1 and 2).

For the treatment of atopic dermatitis, a treatment by a medicament depending on the symptom has been employed in combination with removal of factors of causing diseases or exacerbation and skin care, and a topical steroid agent has mainly been used against inflammation. Also, tacrolimus which is a kind of an immunosuppressive agent has recently been used for the treatment of atopic dermatitis. However, these existing medicaments are not necessarily satisfied in the points of safety and side effects. Thus, it has been desired to develop a therapeutic agent for dermatitis not only having effectiveness but also high safety.

It has been known that Compound [I] which is an active ingredient of the present invention has selective phosphodiesterase IV (PDE IV) inhibitory activity, and useful as an agent for prophylaxis and treatment of asthma and the like. (Patent Literatures 1 and 2). However, it has not been reported that said Compound [I] is useful as an agent for treatment of dermatitis such as atopic dermatitis and the like.
Patent Literature 1: EP 748,805 B (p. 2)
Patent Literature 2: EP 848,000 B (p. 2)
Non-Patent Literature 1: Iwamoto et al., J. Leukoc. Biol., Vol. 52, pp. 572-578 (1992)
Non-Patent Literature 2: Frigas et al., J. Allergy Clin. Immunol., Vol. 77, pp. 527-537 (1986)

DISCLOSURE OF THE INVENTION

Problems to be Solved by the Invention

The present invention is to provide a novel topical agent useful for treatment of dermatitis such as atopic dermatitis and the like.

Means to Solve the Problems

The present invention relates to a topical dermatitis treating agent which comprises, as an active ingredient, a compound represented by the following formula [I]:

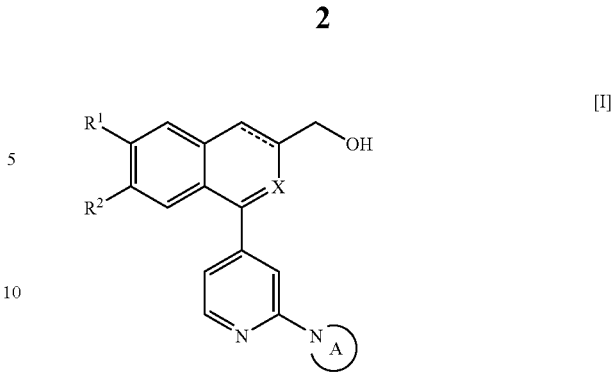

wherein $R^1$ and $R^2$ each represent a lower alkoxy group, =X— represents a group represented by the formula:

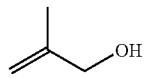

or a group represented by the formula: =N—, Ring A represents a saturated or unsaturated bicyclic nitrogen-containing heterocyclic group having 1 to 4 substituents selected from oxo group, hydroxyl group, a lower alkoxy group, a di-lower alkylaminophenyl group, a pyperidino-lower alkoxy group, a morpholino-lower alkoxy group, a cyclo-lower alkylamino-lower alkylamino group, pyridyl group and morpholino group, and ⁼⁼⁼⁼ represents a single bond or a double bond, or a pharmaceutically acceptable salt thereof.

The present invention also relates to a use of the compound represented by the above-mentioned formula [I] or a pharmaceutically acceptable salt thereof for the manufacture of a preparation to be used for a topical treatment of dermatitis.

The present invention further relates to a method for treating dermatitis which comprises applying a preparation comprising the compound represented by the above-mentioned formula [I] or a pharmaceutically acceptable salt thereof as an active ingredient to affected part.

EFFECTS OF THE INVENTION

The topical dermatitis treating agent of the present invention showed an excellent ear swelling inhibitory effect in a dermatitis model (mouse), so that it is useful for the treatment of dermatitis such as atopic dermatitis and the like. Also, it has a little side effect on a skin (photosensitivity, cytotoxicity and the like), so that it has a characteristic that safety is high as a topical dermatitis treating agent.

BEST MODE TO CARRY OUT THE INVENTION

In Compound [I] which is an active ingredient of the present invention, as the saturated or unsaturated bicyclic nitrogen-containing heterocyclic group represented by Ring A, there may be mentioned, for example, quinolyl group, dihydroquinolyl group, tetrahydroquinolyl group, isoquinolyl group, dihydroisoquinolyl group, tetrahydro-isoquinolyl group, phthalazinyl group, dihydrophthalazinyl group or the like. Of these, tetrahydroquinolyl group or dihydroisoquinolyl group is preferred. Specific examples of the substituents on these heterocyclic group may be mentioned 1 to 4 groups selected from oxo group, hydroxyl group, a lower alkoxy group (methoxy group and the like), a di-lower alkylaminophenyl group (dimethylaminophenyl group and the like), a piperidino-lower alkoxy group (piperidino-ethoxy group and the like), a morpholino-lower alkoxy group (morpholinoethoxy group and the like), a cyclo-lower alkylamino-lower alkylamino group (cyclohexylaminopropyl-amino group and the like), pyridyl group and morpholino group.

As the lower alkoxy group of $R^1$ and $R^2$, there may be mentioned, for example, methoxy group, ethoxy group or the like, and of these, methoxy group is preferred.

Among Compounds [I] which are active ingredients of the present invention, specific examples of the preferred compounds may be mentioned a compound wherein $R^1$ and $R^2$ are methoxy groups, and =X— is a group represented by the formula:

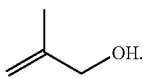

As the other preferred Compound [I], there may be mentioned a compound wherein $R^1$ and $R^2$ are methoxy groups, and =X— is a group represented by the formula: =N—.

Among Compounds [I] which are active ingredients of the present invention, more preferred compounds may be mentioned a compound wherein Ring A is a group represented by the formula:

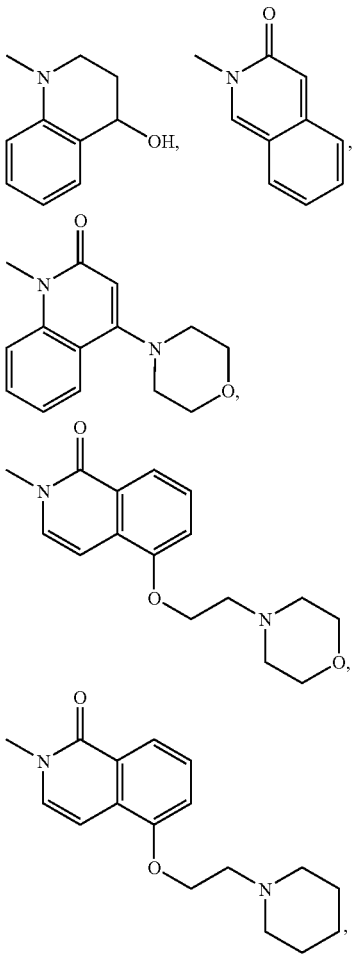

-continued

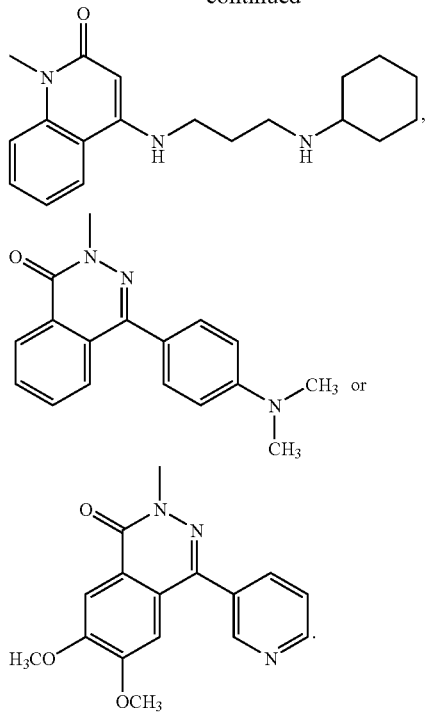

Among the above-mentioned active ingredients according to the present invention, particularly preferred compounds may be mentioned a compound selected from 1-[2-(1,2-dihydro-3-morpholino-2-oxoquinolin-1-yl)pyridin-4-yl]-2,3-bis(hydroxymethyl)-6,7-dimethoxynaphthalene;

1-[2-[1,2-dihydro-5-(2-piperidinoethoxy)-1-oxoisoquinolin-2-yl]pyridin-4-yl]-2,3-bis(hydroxymethyl)-6,7-dimethoxy-naphthalene;

1-[2-[1,2-dihydro-5-(2-morpholinoethoxy)-1-oxoisoquinolin-2-yl]pyridin-4-yl]-2,3-bis(hydroxymethyl)-6,7-dimethoxy-naphthalene;

1-[2-[1,2-dihydro-3-oxoisoquinolin-2-yl]pyridin-4-yl]-2,3-bis(hydroxymethyl)-6,7-dimethoxynaphthalene;

1-[2-(4-hydroxy-1,2,3,4-tetrahydroquinolin-1-yl)pyridin-4-yl]-2,3-bis(hydroxymethyl)-6,7-dimethoxynaphthalene;

1-[2-[(4S)-4-hydroxy-1,2,3,4-tetrahydroquinolin-1-yl]-pyridin-4-yl]-2,3-bis(hydroxymethyl)-6,7-dimethoxy-naphthalene;

1-[2-[(4R)-4-hydroxy-1,2,3,4-tetrahydroquinolin-1-yl]-pyridin-4-yl]-2,3-bis(hydroxymethyl)-6,7-dimethoxy-naphthalene;

1-[2-[1,2-dihydro-4-[3-(cyclohexylamino)propylamino]-2-oxoquinolin-1-yl]pyridin-4-yl]-2,3-bis(hydroxymethyl)-6,7-dimethoxynaphthalene;

1-[2-[4-(dimethylaminophenyl)phthalazin-1(2H)-one-2-yl]-pyridin-4-yl]-2,3-bis(hydroxymethyl)-6,7-dimethoxy-naphthalene;

1-[2-[6,7-dimethoxy-4-(3-pyridyl)phthalazin-1(2H)-one-2-yl]pyridin-4-yl]-2,3-bis(hydroxymethyl)-6,7-dimethoxy-naphthalene; and (3S)-1-[2-[4-(dimethylaminophenyl)phthalazin-1(2H)-one-2-yl]pyridin-4-yl]-3,4-dihydro-3-hydroxymethyl-6,7-dimethoxy-isoquinoline;

or a pharmaceutically acceptable salt thereof.

In Compound [I] which is an active ingredient of the present invention, when it has an asymmetric carbon on the dihydroisoquinoline skeleton or the cyclic group A, there are a plural number of stereoisomers (diastereomeric isomer, optical isomer) based on the asymmetric carbon(s), and both of either one of stereoisomers and a mixture thereof are contained in the active ingredient(s) of the present invention.

Moreover, in Compound [I] which is an active ingredient of the present invention, solvated products such as a hydrate and the like are contained.

As a pharmaceutically acceptable salt of the above-mentioned Compound [I], there may be mentioned, for example, an inorganic salt such as hydrochloride, sulfate and hydrobromide, an organic acid salt such as acetate, fumarate, oxalate, methanesulfonate, maleate and p-toluene-sulfonate.

The topical dermatitis treating agent of the present invention is useful for treatment of atopic dermatitis, contact dermatitis, seborrheic dermatitis, psoriasis, eczema (nummular eczema, autosensitization eczema and the like) and the like.

Also, in Compound [I] which is an active ingredient of the present invention, a compound which does not substantially show toxicity such as local irritation, skin photosensitivity and the like, at least in the range of an effective dose for topical dermatitis treatment. A topical dermatitis treating agent comprising such a compound of the present invention is useful in the point of safety.

The above-mentioned Compound [I] or a pharmaceutically acceptable salt thereof can be obtained by a known method (for example, a method disclosed in EP Patent No. 748,805 or EP Patent No. 848,000: see the following reaction scheme).

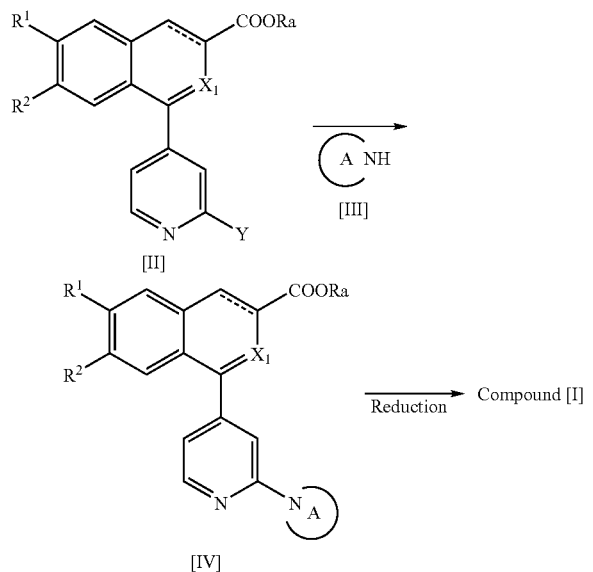

In the above-mentioned reaction scheme, Ra represents a protective group for carboxyl group, =X$_1$— represents a group represented by the formula: =N— or represented by the formula:

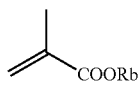

(Rb represents a protective group for carboxyl group) Y represents a halogen atom, and the other symbols have the same meanings as defined above.

As the protective group for the carboxyl group, there may be mentioned, for example, a lower alkyl group and the like.

Among Compound [I] which is an active ingredient of the present invention, a compound wherein Ring A is a group represented by the following formula:

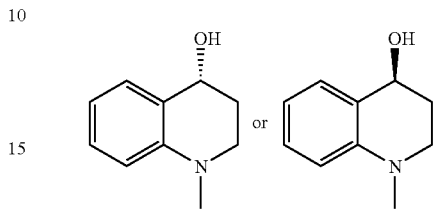

can be prepared, for example, by condensing an optically active tetrahydroquinoline compound represented by the following formula:

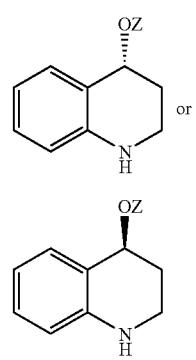

wherein OZ represents a protected hydroxyl group, and Compound [II], reducing said reaction product by sodium borohydride and the like, and then, removing the protective group (for example, tert-butyldimethylsilyl group and the like) for the hydroxyl group from the product.

The above-mentioned optically active tetrahydroquinoline compound [III-a] or [III-b] can be prepared, for example, by subjecting a 4-oxotetrahydroquinoline compound represented by the formula [V]:

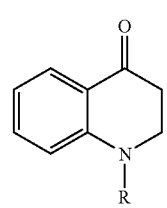

wherein R represents a protective group for amino group, to asymmetric reduction in the presence of a CBS catalyst such as (R)- or (S)-2-methyl-CBS-oxazaborolidine and a hydrogenated boron compound, then, introducing a protective group such as a tert-butyldimethylsilyl group and the like, into the hydroxyl group at the 4-position of the product, and removing the protective group (R) for the amino group. As the protective group for the amino group, there may be mentioned, for example, benzyloxycarbonyl group and the like.

In the topical dermatitis treating agent of the present invention, in addition to Compound [I] or a pharmaceutically acceptable salt thereof which is an active ingredient, an additive for a pharmaceutical preparation such as an absorption enhancer, a pH adjusting agent, a preservative, a flavoring agent, a dispersing agent, a humectant, a stabilizer, a suspending agent, a surfactant and the like, may be formulated alone or in combination of two or more in admixture, if desired.

As the absorption enhancer, there may be mentioned, for example, a monohydric alcohol having 20 or less carbon atoms (ethyl alcohol, isopropyl alcohol, stearyl alcohol and the like), pyrrolidone derivatives (2-pyrrolidone, 1-methyl-2-pyrrolidone and the like), ureas (urea, thiourea and the like), cyclodextrins (α-cyclodextrin and the like), menthol, 1-dodecylazacycloheptan-2-one, calcium thioglycolate, limonene and the like. A content of the absorption enhancer may vary depending on the dosage form, ingredients of the base and the like, and in general, it is desirably 0.1% by weight or more, preferably 0.3% by weight or more for the purpose of effectively producing a absorption-enhancing action, and desirably 10% by weight or less, preferably 5% by weight or less for the purpose of inhibiting side effect.

Specific examples of the pH adjusting agent may be mentioned, for example, an inorganic acid such as hydrochloric acid, sulfuric acid, phosphoric acid and the like, an organic acid such as acetic acid, succinic acid, fumaric acid, malic acid and the like, a metal salt of these acids and the like. An amount of the pH adjusting agent to be formulated may vary depending on the dosage form or ingredients of the base, and in general, it is preferably so formulated that a pH of the preparation becomes 4 to 8.

Specific examples of the preservative may be mentioned, for example, p-hydroxybenzoic acid, methylparaben, chlorobutanol, benzyl alcohol, methyl p-hydroxybenzoate and the like.

Specific examples of the flavoring agent may be mentioned, for example, menthol, rose oil, eucalyptus oil, d-camphor and the like, and specific examples of the dispersing agent may be mentioned, for example, sodium metaphosphate, potassium polyphosphate, silicic acid anhydride and the like.

Specific examples of the humectant may be mentioned, for example, propylene glycol, glycerin, sorbitol, sodium lactate, sodium hyaluronate and the like, and specific examples of the stabilizer may be mentioned, for example, sodium hydrogen sulfite, tocopherol, ethylenediamine tetraacetic acid (EDTA), citric acid and the like.

Specific examples of the suspending agent may be mentioned, for example, tragacanth powder, Gum Arabic powder, bentonite, sodium carboxymethyl cellulose and the like, and specific examples of the surfactant may be mentioned, for example, polyoxyethylene hardened caster oil, sorbitan fatty acid ester such as sorbitan sesquioleate and the like, polyoxyl stearate and the like.

A dermatitis treating agent of the present invention can be used as a topical agent for the purpose of directly administering it to a dermatitis area, and a dosage form thereof may be mentioned, for example, an ointment, a cream, a lotion, a liniment, a cataplasm, a plaster, a patch, a plaster, a liquid and the like.

When the above-mentioned dosage form is an ointment or a cream, an oleaginous base, a water-soluble base, an emulsion base or a suspension base can be used as a base.

As the oleaginous base, there may be mentioned, for example, a hydrocarbon (a hydrocarbon having 12 to 32 carbon atoms, liquid paraffin, white vaseline, squalene, squalane, plastibase and the like), a higher alcohol (an aliphatic monohydric alcohol having 12 to 30 carbon atoms such as lauryl alcohol, cetyl alcohol, stearyl alcohol, oleyl alcohol and the like), a higher fatty acid (a saturated or unsaturated fatty acid having 6 to 32 carbon atoms such as palmitic acid and stearic acid), a higher fatty acid ester (a fatty acid ester such as mirystyl palmitate and stearyl stearate; an ester of a fatty acid having 10 to 32 carbon atoms such as lanolin and carnauba wax, and an aliphatic monohycric alcohol having 14 to 32 carbon atoms; an ester of a saturated or unsaturated fatty acid having 10 to 22 carbon atoms and glycerin, such as glyceryl monolaurate, and its hydrogenated product, and the like), vegetable oil, animal oil and the like.

As the water-soluble base, there may be mentioned, for example, a glycol (ethylene glycol, propylene glycol, polyethylene glycol and the like), and the like.

As the emulsion base, there may be mentioned, for example, an oil-in-water type base, a water-in-oil type base and the like. As the oil-in-water type base, there may be mentioned a base prepared by emulsifying or dispersing a component such as the above-mentioned lanolin, propylene glycol, stearyl alcohol, vaseline, silicone oil, liquid paraffin, glyceryl monostearate, polyethylene glycol and the like, in an aqueous phase in the presence or in the absence of a surfactant, and the like. As the water-in-oil type base, there may be mentioned a base prepared by adding water to a component such as vaseline, a higher aliphatic alcohol, liquid paraffin and the like, in the presence of a nonionic surfactant, and emulsifying or dispersing the mixture, and the like. Also, as the suspension base, there may be mentioned an aqueous base prepared by adding a suspending agent such as starch, glycerin, a high viscosity carboxymethyl cellulose, carboxyvinyl polymer and the like to water to make a gel, and the like.

A dermatitis treatment agent of the present invention can be prepared by a conventionally employed preparation method of a topical preparation. For example, an ointment or a cream can be prepared by mixing and kneading, emulsifying or suspending raw materials of a base depending on the respective dosage form to prepare the base, adding an active ingredient(s) and various kinds of additives, and mixing it in a mixer such as a screw mixer and the like.

The lotion can be used in any form such as a suspension type, emulsion type and solution. As a base for the suspension type lotion, there may be mentioned a mixture of a suspending agent including gums such as gum arabic, gum tragacanth and the like, celluloses such as methyl cellulose, hydroxyethyl cellulose and the like, clays such as bentonite and the like with water, and the like. As a base for the emulsion type lotion, there may be mentioned a base in which water and an oily substance including an aliphatic acid such as stearic acid, oleic acid and the like, a higher alcohol such as stearyl alcohol, cetyl alcohol and the like, are emulsified, and the like. As a base for the solution type lotion, there may be mentioned water and an alcohol such as ethanol, glycerin, propylene glycol and the like. The lotion can be prepared, for example, by adding various base components to purified water, mixing and stirring the same, then, adding an active ingredient(s) and an additive(s) to the mixture, and subjecting to filtration, if necessary.

As a base for the liniment, there may be mentioned, for example, vegetable oils such as olive oil and the like, alcohols such as ethanol, isopropanol and the like, or a mixture of the above with water, and the like. The liniment can be prepared, for example, by dissolving an active ingredient in the base, and adding an additive(s) for a preparation to the mixture if desired and mixing the same.

As a base for a cataplasm, there may be mentioned, for example, water-soluble polymer such as polyacrylic acid, polyvinyl alcohol and polyvinyl pyrrolidone and the like. The cataplasm can be prepared, for example, by mixing an active ingredient, the base and an optionally desired additive(s) for a preparation, heating the same and then cooling.

As a base for the plaster, patch or plaster, there may be used, for example, a support such as non-woven fabric and the like, an elastomer such as natural rubber, isoprene rubber and the like, a filler such as zinc flower, titanium oxide and the like, a tackifier such as a terpene resin and the like, a peeling agent such as vinyl acetate and the like, a softening agent such as liquid paraffin and the like, an anti-aging agent such as dibutylhydroxytoluene (BHT) and the like, in an optional combination thereof. The plaster, patch, plaster and the like can be prepared by the conventional manner such as a solution method, a thermocompression method and the like.

As the solvent for the preparation of the liquid, there may be mentioned, for example, water, ethanol, isopropyl alcohol, benzyl alcohol, polyethylene glycol (PEG400 and the like), propylene glycol, propylene carbonate or a mixture thereof, and the like. Also, said liquid may be used by impregnating with gause, a wound dressing and the like.

An amount of the active ingredient to be formulated into the above-mentioned preparation may vary depending on a form of the preparation, and, for example, in the case of an ointment or a cream, it is preferably 0.0025 to 5% by weight, particularly 0.005 to 0.5% by weight, and in the case of a liquid, it is preferably 0.1 to 200 mg/mL, particularly 0.2 to 20 mg/mL. An administration dose of the dermatitis treating agent of the present invention may be determined depending on a kind or symptom of dermatitis and the like, and a suitable amount of the above-mentioned preparation may be applied to a diseased area once to several times per day.

In the present specification, the term lower alkyl or lower alkoxy means an alkyl or alkoxy having 1 to 6 carbon atoms, preferably an alkyl or alkoxy having 1 to 4 carbon atoms, and cyclo-lower alkyl means a cycloalkyl having 3 to 8 carbon atoms, preferably a cycloalkyl having 3 to 6 carbon atoms.

EXAMPLES

In the following, the present invention is specifically explained by referring to Experiments and the like, but the present invention is not limited by these Experiments and the like.

Experiment (1) Effects of Test Compounds in Contact Dermatitis Model (Method)

BALB/c male mice (BALB/c AnNCrlCrlj, 5-weeks old, acclimating term: one week, body weight: 20 to 30 g, one group: 4 to 6 mice, available from CHARLES RIVER LABORATORIES JAPAN, INC.) were sensitized by epicutaneous application of 100 μL 0.5% (w/v) oxazolone solution (Solvent: acetone) on the shaved abdomen (Day 0). At the 7th day (Day 7) after sensitization, mice were challenged on both sides of right ears by topical application of 20 μL (10 μL for each side) 0.5% (w/v) oxazolone solution containing 1% (w/v) of respective test compounds (Solvent: acetone or an equal amount mixture of acetone/ethanol). Ear thickness was measured before and 24 hours after challenge by using a thickness gauge. In the control group, sensitized animals were challenged with 20 μL 0.5% (w/v) oxazolone solution containing no test compound (Solvent: acetone) on right ears.

(Test Compound)

Test compounds used in this Experiment are shown in the following Tables 1 to 3.

TABLE 1

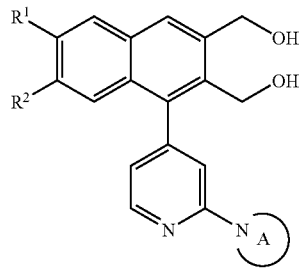

| Compound No. | R$^1$ | R$^2$ | Ring A |
|---|---|---|---|
| (1)* | CH$_3$O— | CH$_3$O— | |
| (2) | CH$_3$O— | CH$_3$O— | |
| (3) | CH$_3$O— | CH$_3$O— | |
| (4) | CH$_3$O— | CH$_3$O— | |
| (5) | CH$_3$O— | CH$_3$O— | |

*Hydrochloride

TABLE 2
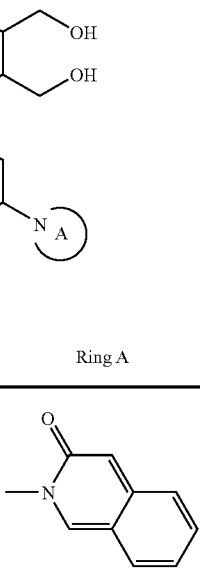
| Compound No. | R¹ | R² | Ring A |
| --- | --- | --- | --- |
| (6) | CH₃O— | CH₃O— | 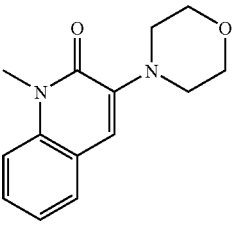 |
| (7) | CH₃O— | CH₃O— | 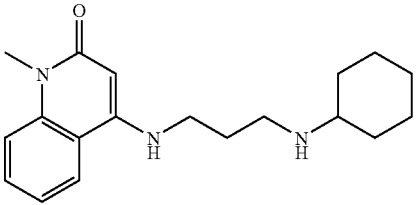 |
| (8) | CH₃O— | CH₃O— | 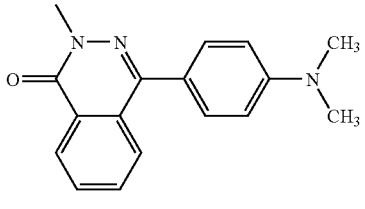 |
| (9) | CH₃O— | CH₃O— | 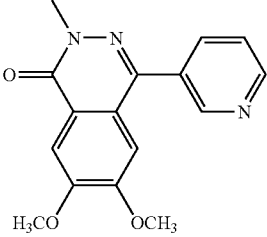 |
| (10) | CH₃O— | CH₃O— | |

TABLE 3

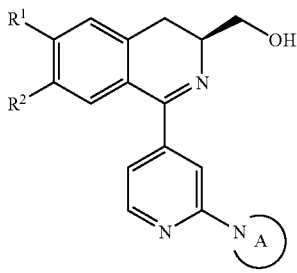

| Compound No. | R¹ | R² | Ring A |
|---|---|---|---|
| (11) | CH₃O— | CH₃O— | (structure shown) |

(Results)

Effects of the respective test compounds were expressed as ear swelling inhibitory rate (%) given by the following formula. The results are as shown in the following Table 4.

Ear swelling inhibitory rate (%)=[1−(mean ear swelling of group treated with test compound/mean ear swelling of control group)]×100

Note) Ear swelling=Ear thickness 24 hours after challenge at Day 7−Ear thickness before challenge at Day 7

(2) Effects of Test Compounds on Dermatitis Models Induced by Repeated Topical Application of Hapten (Method)

At Day 7, BALE/c male mice (BALB/c AnNCrlCrlj, 5-weeks old, acclimating term: one week, body weight: 20 to 30 g, one group: 4 to 6 mice, available from CHARLES RIVER LABORATORIES JAPAN, INC.) were sensitized on both sides of right ears by a topical application of 20 µL (10 µL for each side) 0.5% (w/v) oxazolone solution (Solvent: acetone)(Day−7). At the respective points of the 7th day (Day 0), 9$^{th}$ day (Day 2), 11th day (Day 4), 14th day (Day 7) and 16th day (Day 9) after sensitization, mice were challenged on the both sides of right ears by topical application of 20 µL (10 µL for each side) 0.5% (w/v) oxazolone solution containing 1% (w/v) of the respective test compounds (Solvent: acetone or an equal amount mixture of acetone/ethanol). Ear thickness was measured before challenge of the test compound solution or suspension by using a thickness gauge. At the final day (Day 9), ear thickness was measured also 24 hours after challenge. In control group, sensitized animals were challenged with 20 µL 0.5% (w/v) oxazolone solution containing no test compound (Solvent: acetone) on right ears.

Test Compound:

Compounds described in the above-mentioned Tables 1 to 3 were used.

Results:

Effects of the respective test compounds were expressed as ear swelling inhibitory rate (%) given by following formula. The results are as shown in Table 4.

Ear swelling inhibitory rate (%)=[1−(mean ear swelling of group treated with test compound/mean ear swelling of control group)]×100

Note) Ear swelling=(Thickness of ear 24 hours after final challenge at Day 9)−(Thickness of ear before sensitization at Day−7)

TABLE 4

| | Ear swelling inhibitory rate (%) | |
|---|---|---|
| Test compound (Compound No.) | Contact dermatitis model | Dermatitis model induced by repeated application of Hapten |
| (1) | 74.0 | 50.0 |
| (2) | 74.0 | 47.0 |
| (3) | 74.0 | 55.0 |
| (4) | 78.0 | 53.0 |
| (5) | 75.0 | 50.0 |
| (6) | 75.0 | 51.0 |
| (7) | 68.0 | 49.0 |
| (8) | 75.0 | 37.0 |
| (9) | 52.0 | 60.0 |
| (10) | 66.0 | — |
| (11) | 69.0 | 51.0 |

Preparation Example 1

(1) 200 mL of a toluene solution containing 20.00 g of 1-(2-bromo-4-pyridyl)-2,3-bis(methoxycarbonyl)-6,7-dimethoxy-naphthalene was sonicated under reduced pressure, then, 975 mg of palladium acetate, 1009 mg of tri-tert-butyl-phosphonium tetrafluoroborate, 13.72 g of (4S)-4-(tert-butyldimethylsilyloxy)-1,2,3,4-tetrahydroquinoline and 6.26 g of sodium tert-butoxide were added to the mixture under room temperature, and after replacing the atmosphere with nitrogen, the mixture was stirred at 100° C. for 4 hours. After cooling the mixture by allowing to stand, 100 mL of a saturated aqueous ammonium chloride solution, 100 mL of water and 100 mL of ethyl acetate were added to the reaction mixture, and said mixture was filtered with Celite. Celite was washed with 100 mL of ethyl acetate, and the organic layer was separated. Said organic layer was washed with 100 g of 20% saline solution, dried over anhydrous magnesium sulfate and then concentrated. The resulting residue was purified by column chromatography on silica gel (n-hexane:ethyl acetate=5:1 to 4:1) to obtain 22.31 g (Yield: 80%) of 1-[2-[(4S)-4-(tert-butyldimethyl-silyloxy)-1,2,3,4-tetrahydroquinolin-1-yl]-4-pyridyl]-2,3-bis(methoxycarbonyl)-6,7-dimethoxynaphthalene.

MS (APCI) m/z: 643 [M+H]⁺

$[\alpha]_D^{28}$=−62° (methanol, c=1)

(2) To 212 mL of a tetrahydrofuran solution containing 21.21 g of the compound obtained in the above-mentioned (1) was added 8.74 g of sodium borohydride at room temperature, and then, 16.9 mL of methanol was added dropwise to the mixture at 60° C. over 2 hours. To said reaction mixture was further added 8.74 g of sodium borohydride at the same temperature, and 16.9 mL of methanol was added dropwise to the mixture over 2 hours. After cooling the mixture by allowing to stand, 212 g of 20% saline solution was added to the reaction mixture, and the mixture was extracted with 212 mL of ethyl acetate. The aqueous layer was extracted with 212 mL of ethyl acetate, the organic layers were combined and washed with 212 g of 20% saline solution, dried over 10.6 g of anhydrous magnesium sulfate, and concentrated under reduced pressure. The resulting residue was purified by column chromatography on silica gel (Solvent; n-hexane/ethyl acetate=1/1 to 2/1) to obtain 17.86 g (Yield: 92%) of 1-[2-[(4S)-4-(tert-butyldimethyl-silyloxy)-1,2,3,4-tetrahydroquinolin-1-yl]-4-pyridyl]-2,3-bis(hydroxymethyl)-6,7-dimethoxynaphthalene.

MS (APCI) m/z: 587 [M+H]$^+$
$[\alpha]_D^{28}$=−77° (methanol, c=1)

(3) To 17.00 g of the compound obtained by the above-mentioned (2) were added 8.3 mL of acetic acid and 289 mL of 1M tetrabutyl ammonium fluoride-tetrahydrofuran solution in a water-bath, and the mixture was stirred at room temperature for 4 hours. To the reaction mixture was further added 145 mL of 1M tetrabutyl ammonium fluoride-tetrahydrofuran solution at room temperature, and the mixture was stirred at the same temperature for 2 hours. To the reaction mixture were added 6% aqueous sodium hydrogen carbonate solution and 25% saline solution, and extracted with ethyl acetate. The extract was dried over anhydrous magnesium sulfate, filtered and the filtrate was concentrated under reduced pressure. The resulting residue was purified by column chromatography on silica gel (Solvent; chloroform/methanol=99/1 to 96/4) to obtain 10.4 g (Yield: 72%) of 1-[2-[(4S)-4-hydroxy-1,2,3,4-tetrahydroquinolin-1-yl]-4-pyridyl]-2,3-bis(hydroxymethyl)-6,7-dimethoxy-naphthalene as a crude product. To 30.6 mL of an ethanol solution containing 10.2 g of said compound was added 10.6 mL of water at 40° C. After precipitation of crystals, 306 mL of water was added to the mixture to cool the same. Precipitated crystals were collected by filtration, washed with 20.6 mL of water, and dried at room temperature under reduced pressure to obtain 8.66 g (Yield: 85%, Optical purity: 99.9% ee) of 1-[2-[(4S)-4-hydroxy-1,2,3,4-tetra-hydroquinolin-1-yl]-4-pyridyl]-2,3-bis(hydroxymethyl)-6,7-dimethoxynaphthalene as crystals.

MS (APCI) m/z: 493 [M+H]$^+$
$[\alpha]_D^{22}$=−92.2° (methanol, c=1)

Preparation Example 2

Corresponding starting compounds were treated in the same manner as in Preparation example 1 to give 1-[2-[(4R)-4-hydroxy-1,2,3,4-tetrahydroquinolin-1-yl]-4-pyridyl-2,3-bis(hydroxymethyl)-6,7-dimethoxynaphthalene.

Reference Example (1) In 20 mL of tetrahydrofuran was dissolved 5.04 g of 2,3-dihydro-4-quinolone at 25° C., then, to the solution were added 5.6 mL of benzyloxycarbonyl chloride, 15 mL of water and 4.73 g of potassium carbonate under ice-cooling, and said mixture was stirred at 25° C. for 24 hours. Ethyl acetate was added to the reaction mixture, and the organic layer was separated, dried over anhydrous magnesium sulfate, and then, filtered. The filtrate was concentrated, and the residue was dissolved in 35 mL of isopropyl alcohol under heating. Said solution was gradually cooled, and the precipitated crystals were collected by filtration under ice-cooling. The resulting crystals were washed with 25 mL of cold isopropyl alcohol, and dried at 50° C. for 16 hours to obtain 8.98 g (Yield: 93%) of 1-benzyloxycarbonyl-2,3-dihydro-4-quinolone.

MS (APCI) m/z: 282 [M+H]$^+$
IR (ATR) v=1708, 1683 cm$^{-1}$ (2) To a mixture comprising 1.0 mL of a (R)-2-methyl-CBS-oxazaborolidine solution and 5 mL of tetrahydrofuran was added dropwise 1.4 mL of 1.0M borane•tetrahydrofuran complex at 25° C., and the mixture was stirred at the same temperature for 15 minutes. To said reaction mixture was added dropwise 7 mL of a tetrahydrofuran solution containing 281 mg of the compound obtained in the above-mentioned (1) over 5 minutes. After adding 1 mL of methanol dropwise to the reaction mixture, the mixture was concentrated under reduced pressure, and 10 mL of dichloromethane and 10 mL (pH 4.0) of a phthalate buffer were added to the residue. The aqueous layer was removed from said mixture, and then, water was added to the same. The organic layer was collected by separation, dried over anhydrous magnesium sulfate, and then, filtered. The filtrate was concentrated, and the resulting residue was purified by column chromatography on silica gel (Solvent; hexane/ethyl acetate=2:1) to obtain 283 mg (Yield: quantitative, Optical purity: 97% ee) of (4S)-1-benzyloxycarbonyl-4-hydroxy-1,2,3,4-tetrahydroquinoline.

MS (APCI) m/z: 301 [M+H]$^+$
IR (ATR) v=3417, 1686 cm$^{-1}$ (3) To 424 mL of a dimethylformamide solution containing 28.33 g of the compound obtained in the above-mentioned (2) were added 40.85 g of imidazole and 45.22 g of tert-butyldimethylsilyl chloride at room temperature, and the mixture was stirred at the same temperature for 1 hour. The reaction mixture was concentrated, and then, 280 mL of ethyl acetate and 140 mL of water were added to the residue to wash the same. The organic layer was washed with 140 mL of 10% aqueous citric acid solution, 140 mL of 3% aqueous sodium hydrogen carbonate solution and 57 mL of 20% saline solution, dried over anhydrous magnesium sulfate, and filtered. The filtrate was concentrated under reduced pressure to obtain 39.28 g (Yield: 98.8%) of (4S)-1-benzyl oxycarbonyl-4-tert-butyldimethylsilyloxy-1,2,3,4-tetra-hydroquinoline.

(4) To 393 mL of an ethanol solution containing 39.28 g of the compound obtained in the above-mentioned (3) was added 1.96 g of palladium carbon under nitrogen atmosphere, and the mixture was stirred under hydrogen atmosphere for 4 hours. The reaction mixture was filtered, and the filtrate was concentrated. The resulting residue was purified by column chromatography on silica gel (Solvent; n-hexane/ethyl acetate=30/1 to 20/1) to obtain 14.82 g (Yield: 56.9%, Optical purity: 98.8% ee) of (4S)-4-tert-butyldimethylsilyloxy-1,2,3,4-tetrahydroquinoline.

$[\alpha]_D^{28}$=128.6° (methanol, c=1.10)

UTILIZABILITY IN INDUSTRY

The topical dermatitis treating agent of the present invention shows excellent ear swelling inhibitory effect in dermatitis model so that it is useful for treatment of dermatitis such as atopic dermatitis, contact dermatitis and the like.

The invention claimed is:
1. A method of treating dermatitis which comprises applying a preparation comprising the compound represented by the following formula [I]:

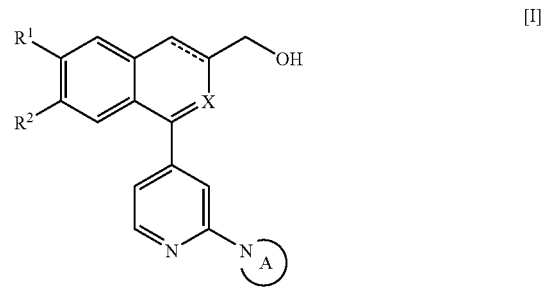

wherein R¹ and R² each represent a lower alkoxy group,
=X— represents a group represented by the formula:

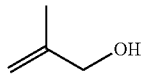

or a group represented by the formula: =N—, Ring A represents a saturated or unsaturated bicyclic nitrogen-containing heterocyclic group having 1 to 4 substituents selected from hydroxyl group, oxo group, a lower alkoxy group, a di-lower alkylaminophenyl group, a pyperidino-lower alkoxy group, a morpholino-lower alkoxy group, a cyclo-lower alkylamino-lower alkylamino group, pyridyl group and morpholino group, and ═══ represents a single bond or a double bond, or a pharmaceutically acceptable salt thereof as an active ingredient to an affected part.

2. The method of treating dermatitis according to claim 1, wherein the saturated or unsaturated bicyclic nitrogen-containing heterocyclic group is quinolyl group, dihydroquinolyl group, tetrahydroquinolyl group, isoquinolyl group, dihydroisoquinolyl group, tetrahydroisoquinolyl group, phthalazinyl group or dihydrophthalazinyl group.

3. The method of treating dermatitis according to claim 1, wherein R¹ and R² are methoxy groups, and =X— is a group represented by the formula:

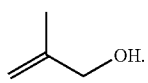

4. The method of treating dermatitis according to claim 1, wherein R¹ and R² are methoxy groups, and =X— is a group represented by the formula: =N—.

5. The method of treating dermatitis according to claim 1, wherein Ring A is a group represented by the formula:

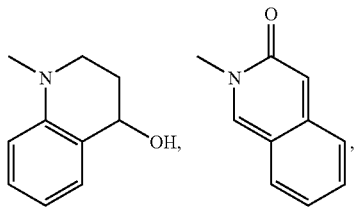

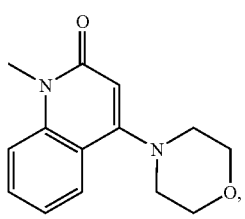

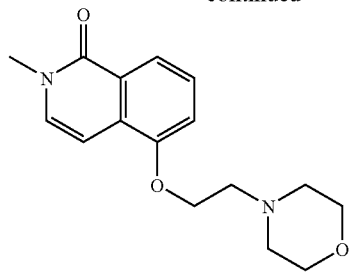

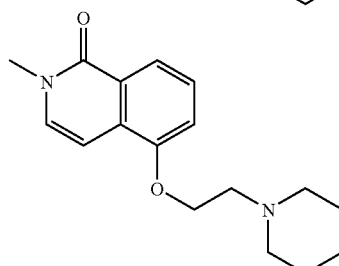

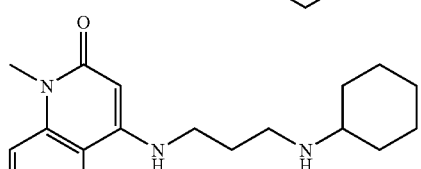

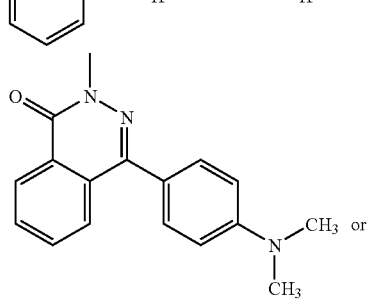

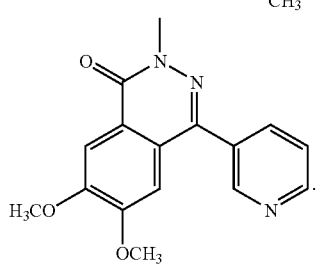

6. The method of treating dermatitis according to claim 1, wherein the agent is a treating agent for atopic dermatitis, contact dermatitis, seborrheic dermatitis, psoriasis or eczema.

7. A method of treating dermatitis which comprises applying a preparation comprising the compound selected from
  1-[2-(1,2-dihydro-3-morpholino-2-oxoquinolin-1-yl)pyridin-4-yl]-2,3-bis(hydroxymethyl)-6,7-dimethoxynaphthalene;
  1-[2-[1,2-dihydro-5-(2-piperidinoethoxy)-1-oxoisoquinolin-2-yl]pyridin-4-yl]-2,3-bis(hydroxylmethyl)-6,7-dimethoxynaphthalene;
  1-[2-[1,2-dihydro-5-(2-morpholinoethoxy)-1-oxoisoquinolin-2-yl]pyridin-4-yl]-2,3-bis(hydroxylmethyl)-6,7-dimethoxynaphthalene;

1-[2-1,2-dihydro-3-oxoisoquinolin-2-yl]pyridin-4-yl]-2,3-bis(hydroxymethyl)-6,7-dimethoxynaphthalene;

1-[2-(4-hydroxy-1,2,3,4-tetrahydroquinolin-1-yl)pyridin-4-yl]-2,3-bis(hydroxymethyl)-6,7-dimethoxynaphthalene;

1-[2-[(4S)-4-hydroxy-1,2,3,4-tetrahydroquinolin-1-yl]pyridin-4-yl]-2,3-bis(hydroxymethyl)-6,7-dimethoxynaphthalene;

1-[2-[(4R)-4-hydroxy-1,2,3,4-tetrahydroquinolin-1-yl]pyridin-4-yl]-2,3-bis(hydroxymethyl)-6,7-dimethoxynaphthalene;

1-[2-1,2-dihydro-4-[3-(cyclohexylamino)propylamino]-2-oxoquinolin-1-yl]pyridin-4-yl]-2,3-bis(hydroxymethyl)-6,7-dimethoxynaphthalene;

1-[2-[4-(dimethylaminophenyl)phthalazin-1(2H)-one-2-yl]pyridin-4-yl]-2,3-bis(hydroxymethyl)-6,7-dimethoxynaphthalene;

1-[2-[6,7-dimethoxy-4-(3-pyridyl)phthalazin-1(2H)-one-2-yl]pyridin-4-yl]-2,3-bis(hydroxylmethyl)-6,7-dimethoxynaphthalene; and (3S)-1-[2-[4-(dimethylaminophenyl)phthalazin-1(2H)-one-2-yl]pyridin-4-yl]-3,4-dihydro-3-hydroxymethyl-6,7-dimethoxyisoquinoline or a pharmaceutically acceptable salt thereof as an active ingredient.

8. The method of treating dermatitis according to claim 7, wherein the agent is a treating agent for atopic dermatitis, contact dermatitis, seborrheic dermatitis, psoriasis or eczema.

* * * * *